United States Patent [19]

Linder et al.

[11] 4,021,492

[45] May 3, 1977

[54] DIBROMINATION PROCESS

[75] Inventors: Jerome Linder, Westfield; William J. Houlihan, Mountain Lakes, both of N.J.

[73] Assignee: Sandoz, Inc., E. Hanover, N.J.

[22] Filed: Nov. 12, 1975

[21] Appl. No.: 630,971

Related U.S. Application Data

[63] Continuation-in-part of Ser. No. 561,484, March 24, 1975, abandoned.

[52] U.S. Cl. .......................... 260/592; 260/515 A; 424/317
[51] Int. Cl.² ............................................ C07C 49/80
[58] Field of Search ................................... 260/592

[56] References Cited

UNITED STATES PATENTS

| | | | |
|---|---|---|---|
| 3,819,706 | 6/1974 | Mehta | 260/592 |
| 3,870,751 | 3/1975 | Houlihan et al. | 260/592 |
| 3,962,342 | 6/1976 | Linder et al. | 260/592 |

OTHER PUBLICATIONS

House, "Modern Synthetic Reactions", 2nd Ed., pp. 478–483 (1973).
Fieser et al., "Organic Chemistry", pp. 655–656 (1944).

*Primary Examiner*—James O. Thomas
*Assistant Examiner*—James H. Reamer
*Attorney, Agent, or Firm*—Gerald D. Sharkin; Robert S. Honor; Timothy G. Rothwell

[57] ABSTRACT

The $\alpha,\alpha$-dibromo-substituted or unsubstituted-4-pivaloyl toluenes, e.g., $\alpha,\alpha$-dibromo-4-pivaloyl toluene, are prepared by bromination of a corresponding p-pivaloyl toluene with liquid bromine at a temperature of at least 125° C.

4 Claims, No Drawings

DIBROMINATION PROCESS

This application is a continuation-in-part of copending application Ser. No. 561,484 filed Mar. 24, 1975 now abandoned.

This invention relates to α,α-dibromo-substituted or unsubstituted-4-pivaloyl toluenes. In particular, it relates to a process for preparing α,α-dibromo-4-pivaloyl toluenes, which are useful as intermediates in the preparation of compounds having pharmaceutical activity.

In the conventional method of carrying out the bromination of p-pivaloyl toluenes, a brominating agent is employed in the presence of an inert organic solvent and a free radical initiator, and certain amounts of by-product are obtained. If a free radical initiator is not employed, low yields are obtained at moderate temperatures; and if a free radical initiator is employed, the reaction takes extended periods of time, on the order of several hours, in order to obtain reasonable yields.

It has now been found that when the bromination process is carried out by adding liquid bromine without either an inert organic solvent or free radical initiator at a temperature of at least 125° C., the amount of undesirable by-product is significantly decreased, whereas the purity of the desired α,α-dibromo-4-pivaloyl toluene is significantly increased, the latter being a totally unexpected result, and the time required to run the reaction is minimal.

The present invention, accordingly, provides an improved process for preparing compounds of the formula:

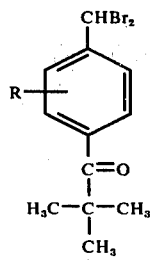

where R represents hydrogen or halo having an atomic weight of about 19 to 36,
which comprises treating a compound of the formula:

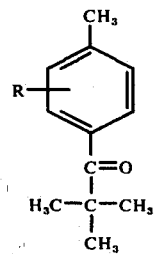

where R is ad defined above, with liquid bromine, the improvement comprising the addition of liquid bromine without an inert organic solvent or a free radical initiator. The mole ratio of liquid bromine to a compound of the formula (II) preferably is 2–2.5:1. The temperature of the reaction is critical in that the bromination process should be carried out at a temperature of at least 125° C., preferably from about 125° to 75° C., especially from about 140° to 165° C. It is also preferred that the liquid bromine be added cautiously, e.g., dropwise, over a period of 30 minutes to 2 hours, preferably 30 minutes to 1 hour. After the addition of the liquid bromine is completed, the reaction mixture is preferably stirred for an additional 10 minutes to 2 hours, in particular, 10 minutes to 1 hour, especially 30 minutes to 45 minutes. The product is recovered using conventional techniques, e.g., evaporation.

The compounds of formula (I) are used to prepare substituted or unsubstituted-4-pivaloyl benzoic acids in accordance with the following reaction scheme:

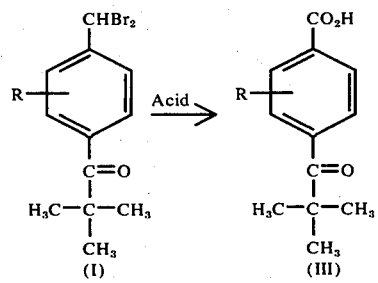

where R is as defined above.

The compounds of formula (III) are prepared by treating compounds of the formula (I) with a mineral acid hydrochloric acid, sulfuric acid or phosphoric acid, preferebly sulfuric acid, in the presence of water. The temperature of the reaction is not critical, but it is preferred that the process be carried out at a temperature between about 50° to 100° C., especially 90° to 110° C. For optimum results, the reaction is run from about 10 to 35 hours, preferably from about 15 to 25 hours. The product is recovered by conventional techniques, e.g., crystallization.

Many of the compounds of formula (II) are known and may be prepared by methods disclosed in the literature. The compounds of formula (II) not specifically disclosed may be prepared from known starting materials by analogous methods.

The compounds of formula (III) are useful because they possess pharmacological activity in animals. In particular, the compounds of formula (III) are useful as anti-obesity agents in the treatment of obesity and antidiabetic agents useful in the treatment of diabetes as indicated by 1) preventing an increase in the blood sugar level in male Wistar rats in groups of 4 which have fasted for 16 hours and then are given an initial dose of 200 milligrams per kilogram of animal body weight of the test compound orally. One hour later, the rats are given 2 grams per kilogram of animal body weight of maltose load. Fifteen minutes after administration of the maltose, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparinized blood is used to determine the blood sugar level with an autoanalyzer. The blood sugar content is compared to the control group which receives 0.5% carboxmethyl cellulose and are run concurrently, and by 2) preventing an increase in the blood sugar level in male Wistar rats in groups of 4 which are fasted for 16 hours and then are given an initial dose of 200 milligrams per kilogram of animal body weight of the test compound orally. One hour later, the rats are given 2.5 grams per kilogram of animal body weight of starch load. Thirty minutes after administration of the starch, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparintized blood is used to determine the blood sugar level with an autoanalyzer. The blood sugar content is compared to the control group which receives 0.5% carboxymethyl cellulose and are run concurrently. The blood sugar levels are calculated and compared to the control.

The compounds of formula (III) are also useful as hypolipidemic agents, particularly as hypolipoproteinemic agents as indicated by the fall in cholesterol and triglyceride levels in male albino Wistar rats weighing 110 to 130 g. initially. The rats are maintained on drug-free laboratory chow diet for seven days and then divided into groups of 8 to 10 animals. Each group with the exception of the control is then given orally 30 to 250 milligrams per kilogram of body weight per diem of the compound of the compound for 6 days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, E., and Lederer, H., 1965, Technicon Symposium, Mediad, Inc., New York, 345–347), are added, and the mixture is shaken for one hour. Cholesterol and triglyceride levels are determined simultaneously on the same sample by Technicon N 24 A (cholesterol) and N 78 (triglyceride) methology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such uses, the compounds of formula (III) may be administered orally or parenterally as such or admixed with conventional pharmaceutical carriers.

The anti-obesity effective dosage of active ingredient employed for the treatment of obesity and the anti-diabetic effective amount of active ingredient employed in the treatment of diabetes may vary depending on the particular compound employed, the mode of administration and the severity of the condition being treated. However, in general, satisfactory results are obtained for both the anit-obesity effect and the anit-diabetic effect when the compounds of formula (III) are administered at a daily dosage of from about 1 milligram to about 200 milligrams per kilogram of animal body weight, p.o., preferably given in divided doses two to four times a day, or in sustained release form. For most large mammals, the total daily dosage for both indications is from about 75 to about 1500 milligrams. Dosage forms suitable for internal use comprise from about 20 to about 750 milligrams of the active compound in intimate admixture with a solid or liquid pharmaceutically acceptable carrier or diluent.

The hypolipidemic effective dosage of compounds (III) employed in the alleviation of lipidemia may vary depending on the particular compound employed and the severity of the condition being treated. However, in general, satisfactory results are obtained when the compounds of formula (III) are administered at a daily dosage of from about 4.0 milligrams to about 250 milligrams per kilogram of animal body weight, preferably given in divided doses two to four times a day, or in sustained release form. For most large mammals, the total daily dosage is from about 300 milligrams to about 2500 milligrams. Dosage forms suitable for internal use comprise from about 75 to about 1250 milligrams of the active compound in intimate admixture with a solid or liquid pharmaceutically acceptable carrier or diluent.

A representative formuation suitable for oral administration is a tablet or capsule prepared by standard tabletting or encapsulating techniques which contains the following and may be administered 2 to 4 times a day in the treatment of obesity, diabetes or lipidemia.

| Ingredient | Weight (mg.) tablet | capsule |
|---|---|---|
| p-pivaloyl benzoic acid | 100 | 100 |
| tragacanth | 10 | — |
| lactose | 247.5 | 300 |
| corn starch | 25 | |
| talcum | 15 | |
| magnesium stearate | 2.5 | |
| Total | 400 mg. | 400 mg. |

EXAMPLE 1

α,α-dibromo-4-pivaloyl toluene.

To a flask equipped with stirrer, thermometer, condenser, addition funnel and heating mantle, there is added 44.0 g. (0.25 mole) of p-pivaloyl toluene at a temperature of 160° C. There is then added dropwise, while maintaining the temperature of 160° C., 88 g. (0.55 mole) bromine over a period of 30 minutes to 1 hour. The mixture is then stirred for an additional 30 minutes at 160° C. The oil is degassed with nitrogen which solidifies at room temperature to obtain α,α-dibromo-4-pivaloyl toluene, m.p. 65° to 68° C.

Following the above procedure and using in place of 4-pivaloyl toluene an equivalent amount of
 a. 2-chloro-4-pivaloyl toluene, or
 b. 2-fluoro-4-pivaloyl toluene,
there is obtained
 a. α,α-dibromo-2-chloro-4-pivaloyl toluene, or
 b. α,αdibromo-2-fluoro-4-pivaloyl toluene, respectively.

EXAMPLE 2

α,α-Dibromo-4-pivaloyl toluene.

To a flask equipped with stirrer, thermometer, addition funnel and heating mantle, there is added 44.0 g. (0.25 mole) of p-pivaloyl toluene at a temperature of 125° C. There is then added dropwise, while maintaining the temperature at 125° C., 95 g. (0.60 mole) bromine over a period of 30 minutes to 1 hour. The mixture is then stirred for an additional 30 minutes at 125° C. The oil is degassed with nitrogen which solidifies at room temperature to obtain α,α-dibromo-4-pivaloyl toluene; m.p. 65 to 68° C.

EXAMPLE 3

4-pivaloyl benzoic acid.

To a flask equipped with stirrer, thermometer, condenser, gas inlet tube and heating mantle, there is added 6 g. (0.018 mole) of α,α-dibromo-4-pivaloyl toluene, 25 g. water and 3 ml. of concentrated sulfuric acid. Air is bubbled into the reaction contents and heated to reflux for 20 hours. The resulting solution is cooled and made basic with 50% sodium hydroxide and then extracted with chloroform. The aqueous layer is acidified with hydrochloric acid, filtered and the solid crystallized from benzene to obtain 4-pivaloyl benzoic acid, m.p. 160°–162° C.

Following the above procedure and using in place of α,α-dibromo-4-pivaloyl toluene an equivalent amount of a. α,α-dibromo-2-chloro-4-pivaloyl toluene, or b. α,α-dibromo-2-fluoro-4-pivaloyl toluene, there is obtained a. 2-chloro-4-pivaloyl benzoic acid, or b. 2-fluoro-4-pivaloyl benzoic acid, respectively.

What is claimed is:

1. An improved process for preparing a compound of the formula $$\text{R} - \text{C}_6\text{H}_3(\text{CHBr}_2)(\text{C(=O)C(CH}_3)_3)$$

where R represents hydrogen, halo having an automic weight of about 19 to 36, which comprises adding liquid bromine to a compound of the formula $$\text{R} - \text{C}_6\text{H}_3(\text{CH}_3)(\text{C(=O)C(CH}_3)_3)$$

at a mole ratio of 2–2.5:1 at a temperature from about 125° to 175° C.

2. A process according to claim 1 which is carried out at a temperature of from about 125° to 175° C.

3. A process according to claim 1 which is carried out at a temperature of from about 140° to 165° C.

4. A process according to claim 3, in which the bromine is added over a period of 30 minutes to 1 hour.

* * * * *